United States Patent [19]

Susi

[11] Patent Number: 4,729,383

[45] Date of Patent: Mar. 8, 1988

[54] METHOD AND APPARATUS FOR AUTOMATICALLY DETERMINING BLOOD PRESSURE MEASUREMENTS

[76] Inventor: Roger E. Susi, 3061 West Albany, Broken Arrow, Okla. 74012

[21] Appl. No.: 679,441

[22] Filed: Dec. 7, 1984

[51] Int. Cl.$^4$ ............................................. A61B 5/02
[52] U.S. Cl. ....................................... 128/681; 128/680
[58] Field of Search .................. 128/672, 677, 680–683

[56] References Cited

U.S. PATENT DOCUMENTS

| | | | |
|---|---|---|---|
| 4,058,117 | 11/1977 | Kaspari et al. | 128/682 |
| 4,223,681 | 9/1980 | Sherman | 128/672 |
| 4,271,843 | 6/1981 | Flynn | 128/681 |
| 4,273,136 | 6/1981 | Kubo et al. | 128/680 |
| 4,349,034 | 9/1982 | Ramsey | 128/681 |
| 4,360,029 | 11/1982 | Ramsey | 128/681 |
| 4,378,807 | 4/1983 | Peterson et al. | 128/682 X |
| 4,461,266 | 7/1984 | Hood, Jr. et al. | 128/680 X |
| 4,501,281 | 2/1985 | Furukawa | 128/680 |
| 4,543,962 | 10/1985 | Medero et al. | 128/680 X |
| 4,546,775 | 10/1985 | Medero | 128/680 X |

FOREIGN PATENT DOCUMENTS 2092309 8/1982 United Kingdom ................ 128/672

*Primary Examiner*—William E. Kamm
*Assistant Examiner*—Angela D. Sykes
*Attorney, Agent, or Firm*—Head & Johnson

[57] ABSTRACT

A blood pressure monitor which automatically and noninvasively measures a patient's systolic, diastolic, and mean arterial blood pressure. Measurements are based on the oscillometric principle. Cuff pressure oscillations are monitored as cuff pressure decreases from a value higher than systolic pressure, down to a value below diastolic pressure. The oscillometric method is the most widely used clinical method of automated noninvasive blood pressure monitoring. The apparatus utilizes a conventional pressure cuff placed about an extremity of the body of the subject and the pressure of air in the cuff is measured at a very low frequency steady pressure, which is called "cuff pressure". A second measurement, which is the oscillation signal after passing through a band pass filter, gives the oscillations in the wall of the artery about which the cuff is placed. The method utilizes an inflatable occlusive cuff which controls the pressure placed on the artery. The signal information that is diagnostically used is the oscillation period and oscillation amplitude as the cuff pressure is reduced monatonically from a value above the systolic pressure to a value below the diastolic pressure. From this data the subject's blood pressure and heart rate values can be determined.

11 Claims, 7 Drawing Figures

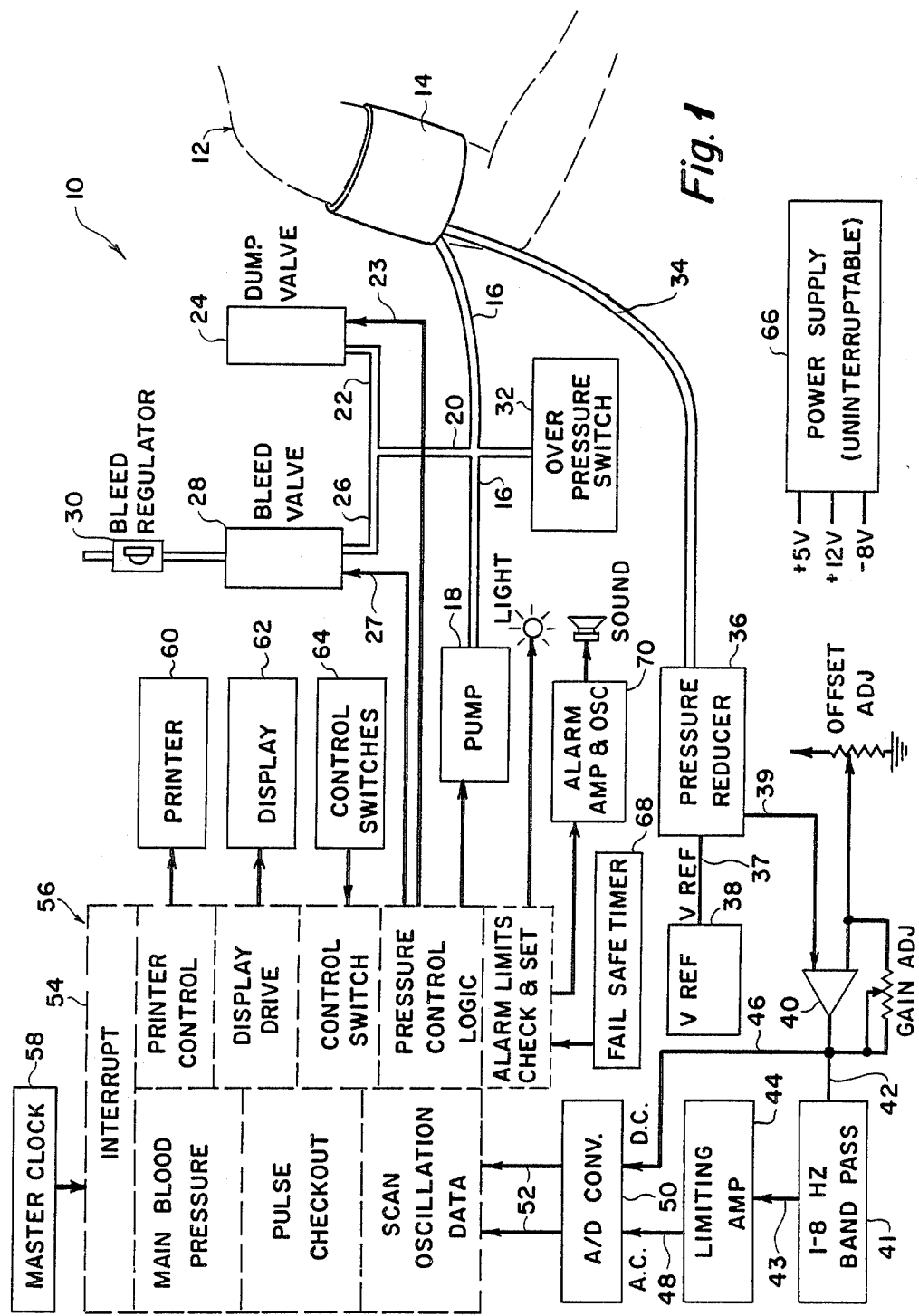

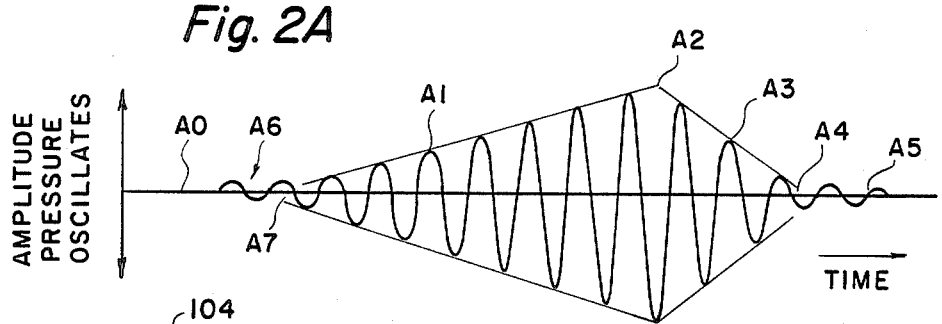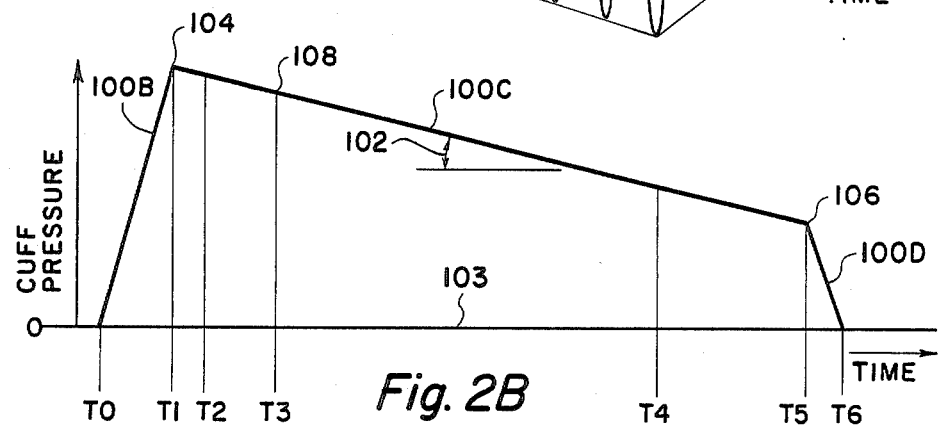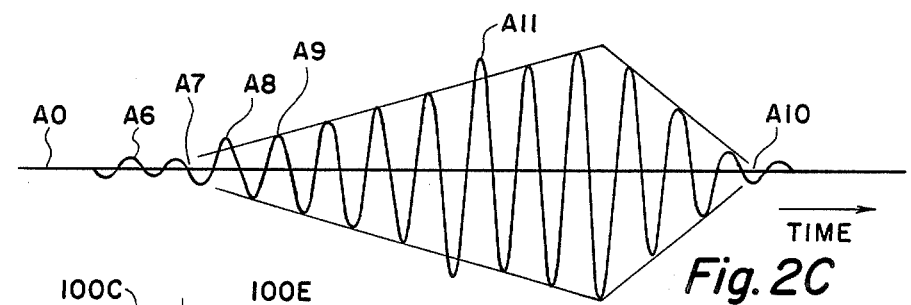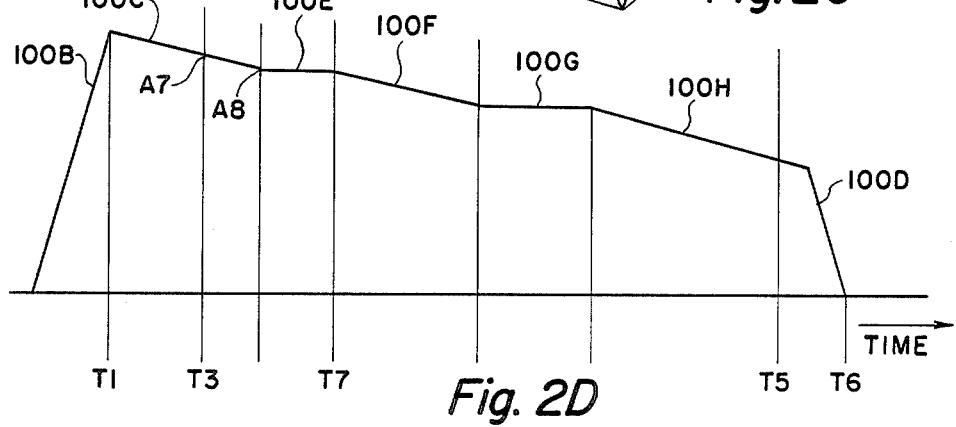

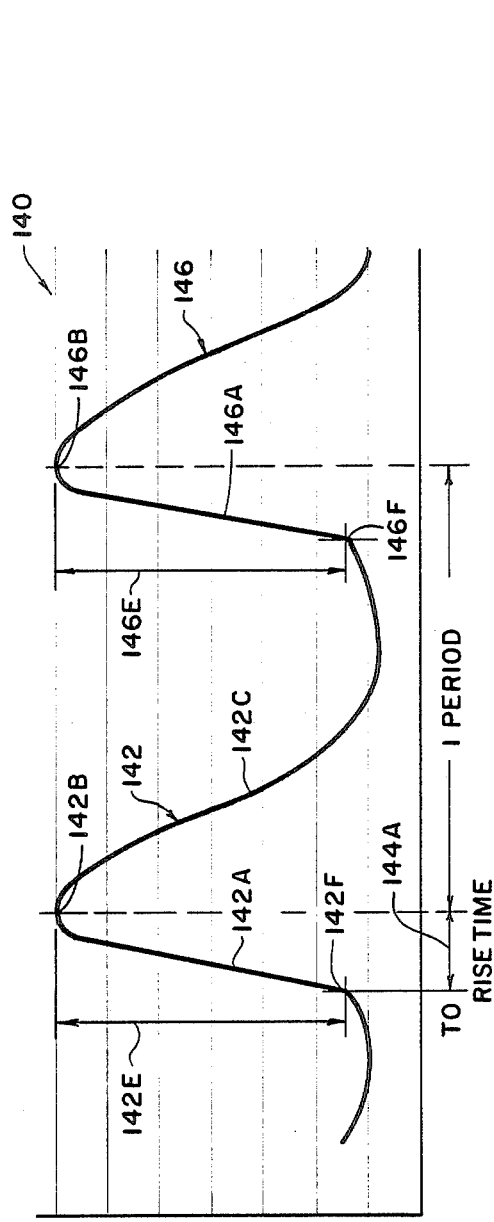
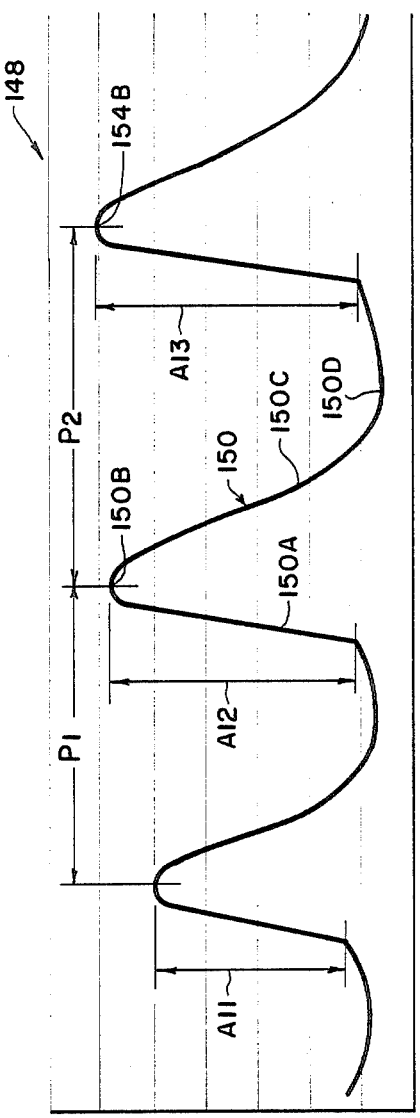

METHOD AND APPARATUS FOR AUTOMATICALLY DETERMINING BLOOD PRESSURE MEASUREMENTS

BACKGROUND OF THE INVENTION

1. Field of the Invention

This invention lies in the field of measurement of the blood pressure of living animals and persons. While it uses the same type of cuff and cuff pressure variations as are used in other methods, it utilizes a more reliable method of determining when the oscillations are valid, and when they are not. That is, when there may be artifacts. More particularly, this invention is related to the measurement of systolic, diastolic, and mean arterial pressures involved, in the blood pressure cycle.

2. Description of the Prior Art

As cuff pressure is reduced, less pressure is applied to the underlying artery. The length of time that the artery is occluded is decreased as the cuff pressure is reduced to just below the systolic pressure, the force of the systolic pressure forces the occluded artery open, and blood flows through the artery in spurts, and the amplitudes of the oscillations increase. In the oscillographic method of measuring blood pressure the systolic pressure magnitude of the oscillations induced into the cuff, changes from a steady state to a constantly increasing magnitude. That is, with reduction in cuff pressure, the artery is open for an increasingly larger portion of the heart time cycle and therefore the oscillations increase as the occluding pressure decreases.

With further decrease in cuff pressure, the amplitudes increase up to a maximum value of amplitude of oscillation and the cuff pressure at the time of this maximum amplitude of oscillation is determined as the mean arterial pressure. This is an indirect method of measurement. However, in the industry, it is taken as a valid definition of mean arterial pressure, and has been proved by very precise experimental procedures.

With continued cuff pressure reduction the underlying artery is open throughout the entire cardiac cycle. The arterial wall movement becomes less and less and the amplitude of the cuff pressure oscillation decreases and then becomes uniform and of small amplitude. The point at which the oscillations stop decreasing and become uniform, is noted as the diastolic pressure.

In the prior art, the system which is most often utilized is one in which the cuff pressure is stepped down in value by equal small increments under control of the apparatus. For each value of cuff pressure, as the value of cuff pressure is monitored a comparison of two independent successive measurements of oscillations is performed to determine whether the oscillation measurements are valid. From the amplitude of cuff pressure and the amplitude of oscillation values, one can determine whether the amplitude of oscillation is increasing as the cuff pressure reduces and determine when it reaches a maximum and then starts to reduce, and reduces at a rate which is greater than the rate at which it increased at the start of the measurements.

With the amplitudes of oscillations as recorded at each level of cuff pressure, depending upon a comparison of the two oscillations, it can be determined whether the measurements are valid or, if not, that there are artifacts, or noise, in the blood system, that are hiding the true details of the amplitude of the oscillation.

SUMMARY OF THE INVENTION

It is a primary object of this invention to provide a method and apparatus which is safe and reliable and has adequate precautions for detecting and disregarding artifacts.

It is a further object to make a series of blood pressure measurements within as short an interval of time as possible. Qualities of reliability and speed are important in many surgical operations where this monitor must be used. In the course of surgical operations, a continual monitoring of the blood pressure is extremely important.

It is therefore an important object of this invention to provide an apparatus and a method which can safely and reliably make the important blood pressure measurements that are required in a rapid manner without sacrificing accuracy or speed.

It is also another object of this invention to make an apparatus by which artifacts in the recorded data can be readily detected and steps taken to disregard those values and repeat the measurements, etc.

These and other objects are realized and the limitations of the prior art are overcome in this invention by using an automatic blood pressure monitor which reliably measures the systolic, diastolic, and mean arterial pressure (M.A.P.). The apparatus provides a pressure cuff similar to those normally utilized in the manual method of taking blood pressure. The cuff is wrapped around an extremity of the body of a person, such as the upper arm, and the cuff is inflated with air to a pressure which is higher than the normal systolic pressure. Means are provided for controlling the flow of air from the cuff by means of a bleed valve of selected rate of pressure drop or a closure of all bleeding of pressure so that the pressure remains constant and a third operation of dumping or opening wide the cuff outlet, so as to reduce the pressure to atmospheric pressure as rapidly as possible.

In the normal hand method of blood pressure measurement a person trained in this measurement will use a stethoscope applied to the distal portion of the artery to hear whatever sounds are made by the pulsations of blood which pass through the artery as the cuff pressure is reduced below the systolic value.

Of course, in an automatic machine it is possible to use an acoustic detection system. However, this invention does not. The detection system of this invention utilizes a means for recording oscillation amplitude and period of blood flow corresponding to one heartbeat. Those oscillations are repeated with each subsequent heartbeat. Successive values of the amplitude and period of the oscillations are noted and compared. If they are within certain permitted tolerances this will indicate that the measurements are valid and therefore the operation can proceed to successive measurements at lower and lower cuff pressures. These values of cuff pressure, and of oscillation amplitude and period, are digitized and recorded under control of a microcomputer and are used to predict subsequent oscillations as the operation goes along. If two successive heartbeats show predictably similar amplitude and period information, then the validity of the measurement is believed to be correct.

As previously mentioned, in the manual operation, the cuff pressure is bled down at a selected rate from a value higher than the systolic pressure down to a value below the diastolic pressure. In the prior art the automatic monitors utilize a step down type of pressure measurement wherein the machine successively drops the amplitude of cuff pressure by a small selected amount so that while the pressure in the cuff is constant, two or more oscillation amplitudes should be identical. However, this is a slow and ponderous type of measurement.

In this invention the cuff pressure is bled down continuously at a selected rate which is under control of a bleed valve. There is also a closure valve to hold the pressure constant and there is also a dump valve which will quickly open the cuff to atmospheric pressure. With the cuff pressure continually dropping due to the bleeding process successive amplitudes will depend upon the normal operation of the blood cycle but also upon the fact that the cuff pressure has been reduced between a first and a second measurement. So a comparison of the amplitudes of two successive pulse oscillations would not be expected to be the same. However, it is possible to calculate what the predictable difference in amplitude of oscillation would be for two oscillations measured successively at two different but closely related cuff pressures. This differential amplitude can be applied to the two amplitudes as measured. If the measured difference is within a selected range, then the two amplitudes are valid measurements and are free of artifacts. If so, then the second amplitude is compared with the third amplitude. If the differential amplitude is correct, then the third amplitude is compared to the fourth, and so on.

Starting with a cuff pressure above systolic, as the pressure bleeds down, at first no blood goes through the artery and there will be relatively small oscillations present. Once the occlusion of the artery is momentarily opened, then a spurt of blood will pass through the artery during this short period and the amplitude will be larger than it was when there was no flow in the artery. Successively as the cuff pressure reduces the amplitude of oscillation will increase.

The value of cuff pressure at the time where the amplitude of oscillation changes from a small constant value to an increasing value, is denoted as the systolic pressure. That is, the value of cuff pressure at which the occlusion of the artery is first broken. The value of cuff pressure at which a maximum value of oscillation is observed is called the mean arterial pressure.

After the mean arterial pressure is reached, then the amplitude of oscillation begins to drop rapidly with further decrease in cuff pressure, until a point is reached at which the oscillations return to a very small value and remain fairly constant thereafter. The point which this reduction in cuff pressure oscillation takes place is called the diastolic pressure. Thus, with one complete operation, starting with a cuff pressure greater than systolic and bleeding down continuously until the point where there is no further reduction in the oscillation amplitude, one complete cycle of blood pressure measurement has been completed, there have been derived three important values of blood pressure, namely, systolic, M.A.P. and diastolic.

BRIEF DESCRIPTION OF THE DRAWINGS

These and other objects and advantages of this invention and a better understanding of the principles and details of the invention will be evident from the following description taken in conjunction with the appended drawings, in which:

FIG. 1 represents a schematic diagram of the major portions of the apparatus of this invention.

FIGS. 2A, 2B, 2C and 2D represent the cuff pressure and the pressure oscillations in the cuff as a function of time during operation of the instrument.

FIG. 3A is a diagram of pressure oscillations in a cuff when the cuff pressure is below the systolic pressure and is stable.

FIG. 3B is a diagram of pressure oscillations in a cuff when the cuff pressure is below the systolic pressure and is being bled down.

DETAILED DESCRIPTION OF THE PREFERRED EMBODIMENT

Referring now to the drawings and in particular to FIG. 1, there is shown in schematic fashion one embodiment of this invention. Before explaining in detail the present invention, it is to be understood that the invention is not limited in application to details of the construction and application and arrangement of parts illustrated in the accompanying drawings. The invention is capable of other embodiments and of being practiced or carried out in a variety of ways. It is to be understood that the phraseology and terminology employed herein is for the purpose of description and not of limitation.

While the apparatus which is designed for the purpose of determining various types of blood pressure measurements upon the body of a living person, it will have essential instrumentation to do what is required and will have additional instrumentation which is for the purpose of unforeseen difficulties and troubles. For example, if the pressure should get higher than is proper, alarm means are provided and there are a number of other measurements which are continually being monitored, to minimize any danger or discomfort to the subject of the measurements. There are other measurements made for the purpose of determining the validity of the results that are being recorded.

It will be clear, of course, that any measurements made directly for the purpose of determining blood pressure is of extreme importance in this instrument and therefore will be described in great detail and will be claimed properly. Other measurements that are made for purposes of safety and other normal types of protections which are provided in this type of instrumentation may not be described in great detail because the invention does not rely on those particular measurements to determine blood pressures although they are present in the instrument. Such things are not specifically claimed.

On quick review, the instrument is designed to measure systolic pressure, diastolic pressure and mean arterial pressure. The specific features of the instrumentation which do this and which also determine the validity of the results being recorded are described in full detail. Others are just indicated in a general way without going into great detail, since they are generally commercial items.

In FIG. 1, a person indicated generally by the numeral 12 is having his blood pressure measurement taken by means of a pressure cuff 14 which is wrapped around a portion of his body such as the upper arm which includes an artery in which the pressure is to be measured. The instrumentation is indicated generally by the numeral 10. Pump means 18 provides air under pressure through line 16 to the cuff 14 to inflate the cuff to a pressure which is higher than the systolic pressure in the artery. When the pressure reaches that value the pump is shut off and a check valve maintains that pressure in the cuff. If the pressure is over a safe value, then it is reduced by an overpressure switch. The pressure in the cuff is transmitted by means of the tubing 16, 20, 22 and 26 to a dump valve 24 and to a bleed valve 28. The purpose of the dump valve is to rapidly remove the pressure of air in the cuff as rapidly as can be done. The bleed valve 28 is for the purpose of bleeding down the pressure at a known and controlled rate. Various rates may be applied by means of a bleed regulator 30. The dump valve and bleed valve are connected by electrical signal on leads 23 and 27 from a pressure control logic which is controlled by a microprocessor or microamplifier and control, shown generally by the numeral 56.

The microcomputer is of commercial make and is for the purpose of monitoring a large number of variables as a function of time and to control other variables in terms of the first variables as necessary, according to carry out the process or as to avoid difficulties of one sort or another. No detail will be given to the microcomputer because any one of many different commercial makes can be used but the component parts such as the pressure control logic, will be a part of the microcomputer and will be entitled means for the control of pressure, and so on. The way which the pressures in the cuff and in the valves and so forth are used will be made clearer in regard to the description of FIGS. 2A, 2B, 2C and 2D.

A separate flexible tubing 34 is connected to the cuff and goes to a pressure reducer 36. The pressure as measured by a pressure transducer goes as an electrical signal over lead 39 to an amplifier 40.

As in the use of pressure gauges for many different kinds of operation, for measuring pressures in relation to the atmosphere, the pressure is recorded in terms of gauge pressure. Inasmuch as the total circuitry varies with age, temperature, etc., an adjustment is provided in the device called the offset adjustment. This adds an additional component of voltage into the amplifier to make the output of the amplifier 40 on leads 42 and 46 the gauge pressure of air in the cuff.

The output of the pressure amplifier 40 goes by lead 42 to a band pass filter 41 which passes frequencies in the range of 1 to 8 Hz. Another component of the pressure in the cuff goes by lead 46 as a substantially constant or slowly varying pressure. In other words, the pressure that is affected directly by the pump is the so-called D.C. pressure and the component that is filtered out of the pressure measurement at 36 is a low frequency alternating pressure in the range of 1 to 8 Hz.

These two values of pressure in the cuff are measured at the same point. One is a D.C. component and one is an A.C. component. The D.C. component is substantially the constant or nearly constant pressure in the cuff and the A.C. component indicates the presence of oscillations in the wall of the artery as the blood in due course passes through the artery in short spurts during small fractions of the heartbeat cycle. So one can speak of a "cuff pressure" by which is intended the D.C. component and can conceive of the amplitude of an oscillation pressure which would be the A.C. component. Both of these components of pressure, the D.C. component going directly through line 46, the A.C. component going through line 42 through the band pass filter 41, through line 43 to a limiting amplifier 44 and through line 48 to an analog-to-digital converter (A/D C). Once these data are digitized, they can be handled, controlled, amplified and stored, displayed and printed very simply. We must remember that there are two components of pressure, a steady component which is the cuff pressure, and the alternating component which is the amplitude of the oscillation set up in the artery.

There will be more description of the apparatus as we proceed. However, for the present, refer to FIGS. 2A, 2B, 2C and 2D. In FIGS. 2A and 2B there are two drawings illustrating in FIG. 2A the amplitude of oscillation pressure (PCA) and in FIG. 2B the amplitude of steady pressure or cuff pressure (PC). Consider FIG. 2B first. There is a zero line 103 of zero pressure and at a selected time T0 the pump 18 is started and the pressure in the cuff increases to a maximum value 104 which is higher than the systolic pressure, but lower than the overpressure value. At time T1, the pump stops because the pressure is high enough, and the bleed valve opens and the pressure starts to reduce along the line 100C at a known rate 102 which is a variable for different conditions of subject and problem. This pressure reduces continuously as long as no difficulties arise and eventually reaches a point 106 at time T5 where the dump valve 24 opens and all air is removed from the cuff as the pressure falls along line 100D, to zero at time T6.

Turning to FIG. 2A, zero line A0 is a reference of amplitude of oscillatin of the pressure signal in line 48 going to the analog to digital converter (A/DC) at time T2 the instrumentation is turned on and a low level of high frequency signal A6 is observed. The period up to A7 is one in which the pressure in the cuff is above systolic.

Systolic pressure is that pressure which corresponds to 108 on the bleed line 100C at the time T3. Once the cuff pressure goes below systolic, then during each heart pulse for a short period of the cycle the blood pressure in the artery is higher than the cuff pressure and, so through a short interval of time the blood is permitted to pass through the artery during the rest of the period between heartbeats the artery is occluded, that is, there is no flow of blood through the artery because in the cycle of pressure of the artery it is reduced below the systolic value and except for a very short interval of time when the occlusion is opened, and blood spurts through and that sudden spurt and stopping of the blood flow causes an oscillation of blood in the artery which is of a frequency within the range of 1 to 8 Hz, and so would be observed as an oscillation starting at A7 and increasing with time according to the oscillation signal A1, up to a maximum value A2. Thereafter, at that maximum value the amplitude reduces according to A3 and at a time A4, or time T5 the amplitude has reduced to a very small value of high frequency A5 which is a noise similar to that indicated as A6 on a beginning end of the diagram. In other words, if there has been no problem with the operation of the instrument, and no unusual noise, the applied pressure follows a very simple cycle from T0 rising to 104 along line 100B and the then bleeding off at a selected pressure drop per second rate, along the curve 100C to the point 106 at T5 which is substantially the end of the oscillation and is taken as the diastolic pressure of the patient. So in this one cycle what has been measured is the systolic pressure at time T3. The maximum oscillation amplitude or mean arterial pressure at time T4, and the diastolic pressure at time T5 along the curve 100C of cuff pressure.

This instrument is unattended and must be provided with built-in safeguards to be sure that the controls operate properly and that the measurements that are made are valid, and so on.

The principal difficulty that occurs is that for one reason or another there is some artifact either a nervous jerk of the arm of the subject or movement of the arm or bumping of the cuff. For one reason or another there is a momentary change of condition that causes one portion of oscillation, one cycle or one-half cycle even, that is different from all the others. If the cycles of oscillation are shown in FIG. 2A, that is a very fine record and it is observed that on the rising amplitude portion A1 each succeeding oscillation is larger by a fixed amount than the preceding one. This is because the cuff pressure has been reduced in the meantime by the bleeding. Therefore a larger spurt of blood can pass through and that causes a larger value of oscillation. However, if the oscillation is due to some artifact, or is what is called a noise, that has nothing to do with particular measurements being made and it must be possible to recognize that it is an artifact and therefore it is to be discarded.

Referring now to FIG. 2C, there is shown one cycle identified as A8 in which the amplitude is higher than it should be in view of the situation in FIG. 2A when everything is free of artifacts and noise. By comparing the half cycle A8 and the preceding one, A7, it is unpredictably larger and so that pulse must be discarded. Considering those two cycles A8 and the preceding one A1 the answer is that A8 is not usable because the preceding cycle would predict lesser amplitude than is seen as A8. In order to prove that this is anomalous, the bleed valve is closed and the computer scans all of these values of amplitude and period when it sees the improper ratio, it stops the bleeding by closing the bleed valve. This maintains a constant cuff pressure 100E for a time until there is an oscillation which matches the predictions or two in a row occur which have equal amplitudes and periods. At time T7, when two such cycles have been observed, the bleeding starts again at the same rate as previously, and this is indicated as 100F and here again for one reason or another, whether the amplitude is higher as indicated by A8, or A11, or the period of the cycle is different, then the computer alerts the bleed valve to close and therefore again the constant cuff pressure 100G is provided, until two more cycles have been shown to have the same period and the proper ratio of amplitude. This procedure is followed through the remaining part of the bleed down of pressure 100H. In other words, if the computer is scanning the values of cuff pressure, and of cuff amplitude of oscillation, and finds that there is an artifact involved in that measurement, it then halts the further bleeding of pressure and maintains the cuff pressure constant until a satisfactory pair of adjacent oscillations are found which have the proper amplitude ratio. The computer then goes back on the bleeding rate, 100H.

Referring now to FIGS. 3A and 3B, there are shown two schematic drawings of the pressure oscillations in the cuff, which are generated when the cuff pressure is less than the systolic pressure. In FIG. 3A the cases shown when the cuff pressure is constant each successive period of the blood pressure cycle should be substantially identical. In the FIGURES the numeral 140 represents generally the appearance of a series of pressure oscillations. Each pressure oscillation starts at a time T0, and a selected level of pressure indicated by the numeral 142F. The pressure rises 142A relatively rapidly to a peak value 142B. The time taken for the pressure to rise from the point 142F to the point 142B is shown as 142A which is called the rise time of the pressure. Past the peak 142B the pressure falls off along the curve 142C down to a low value at 142D and then rising a little bit, starts again at a point 146F corresponding to 142F, and rises rapidly to the peak at 146D.

The amplitude 142E of the pressure is measured between the point 142F and 142B. This curve of pressure as a function of time is measured by a microstrain gauge and converted to an electrical signal which can be amplified and digitized. It is digitized at digital intervals adjustable from 8 to 24 milliseconds and the 8 bit words representing voltage amplitudes are stored in a random access memory, (RAM).

This is only a temporary storage since the numbers are useful only for a short period as the pressure wave shape and magnitude and period are compared with adjacent or successive values. Once the comparison is found to be satisfactory, the data are no longer stored and new data come in to take their place in the memory.

In FIG. 3B there are shown three cycles or periods of the pressure oscillation in the cuff. As the cuff pressure is bled off, that is, the cuff pressure is being reduced at a known selected rate (not shown) and as it becomes lower the amplitudes of the pressure wave will increase as was shown in FIG. 2. Here again the various dimensions of the pressure wave are similar to those which have been described in more detail in connection with FIG. 3A.

In the normal operation of this invention, while the cuff pressure is being bled down, the amplitudes of the pressure oscillation are measured, digitized, stored and then the next period is handled the same way and then the next one, etc. If two successive periods such as the one peaking at 150B and the second one peaking at 154B it is seen that there will be a slight increase in amplitude of the second peak over the first peak. In other words, the second amplitude is larger than the first amplitude by a small amount because the cuff pressure has been reduced. The theory for all of this has been carefully worked out and theoretical equations have been developed which will permit one to calculate for given instantaneous values of cuff pressure and cuff pressure decline, and measures of amplitudes, etc., so that the ratio of the peak amplitude of the successive amplitude, to the first amplitude, will be a certain number greater than one as determined by a solution of the equation made for that particular cuff pressure and amplitude. Having these two waves of the pressure of the signal in storage in a digital memory, it is possible for the computer to calculate the actual ratio of the two amplitudes and if this falls within a certain range of the expected or predicted value, then it is assumed that the values of amplitude are true and correct and that they are not disturbed by an excessive amount of noise.

On the other hand, if there is a large amount of noise, or artifacts as they are known in the art, the data cannot be used, and thus successive measurements have to be made until the amplitude ratios come out to be within the prior range of the expected values.

It will be clear that if these pressure waves, as alternating electrical signals are digitized and stored in a memory, it is possible by checking the actual time that the peak value of 142B, for example, and of 146B, for example, were made, that the period of that heart cycle was a number which is precisely known. Consequently, from the data already in the memory, it is possible to calculate the periods of each of these pressure cycles, and if there are any which are anomalous, those numbers should be thrown out and with pressure bleeding stopped, the measurements are repeated until the period between successive peak values of the pressure oscillations come to be substantially equal.

In the prior art there are other systems which have been built to do measurements of this sort, such as U.S. Pat. No. 4,349,034 which uses a sequence of succeeding pressure drops of small but uniform dimension. By going in steps, the operation takes considerably longer than if it is done by a bleeding method and therefore this instrument is designed to work on a bleeding of cuff pressure. However, it is necessary, of course, to maintain a constant cuff pressure at the value where an artifact is found until the artifact is removed and then the pressure bleeding starts again. As shown in FIG. 1, there are only two ways of controlling the air pressure in the cuff. One is to dump it rapidly with a big valve. Another one is to bleed it at a slow controlled rate with a bleed valve. There are no means in this apparatus for controlling the cuff pressure to go down by uniform pre-selected steps of pressure. The only way it can go down is by dumping or by bleeding. However, means are provided for closing off both valves so that it doesn't dump or it doesn't bleed but it maintains the same cuff pressure until sufficient data have been recorded to prove that the artifact is absent.

Whereas in the prior art cuff pressure is maintained constant to take at least two cycles of oscillation to see if the amplitudes are equal. In this method, by bleeding cuff pressure, it is possible to take any two successive periods to compare.

For example if a series of cycles of pressure oscillation are recorded, amplitude 1 can be compared with amplitude 2. If that comparison is satisfactory, then amplitude 3 is recorded and the comparison is made between amplitude 2 and amplitude 3. If this comparison is satisfactory then amplitude 4 is compared, and so on. In other words, it is only necessary to make one additional amplitude measurement to make a new prediction and subsequent comparison.

Thus, for example, periods of oscillation or 5 heartbeats are all that are necessary to make 4 comparisons. More generally (1+N) periods will make N comparisons; whereas in the prior art it takes (2N) periods to make N comparison. This method of operation can speed up the blood pressure measurements very greatly, by a factor of approximately two to one.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. A method for automatically determining, by noninvasive blood pressure measurements, the mean arterial pressure of a person, comprising the steps of:
   (a) placing a pressure cuff around an extremity of said person's body and inflating said cuff to a selected cuff pressure;
   (b) measuring and storing the amplitude of cuff pressure oscillations (PCA) with each heartbeat of said person;
   (c) bleeding down the cuff pressure at a selected substantially linear rate and recording the first amplitude of oscillation (PCA 1) at a first cuff pressure;
   (d) repeating step (c) for a second lower cuff pressure on the succeeding heartbeat to obtain a second amplitude of oscillation (PCA 2) at a second cuff pressure;
   (e) determining the difference in amplitudes between PCA2 and PCA1, whereby as long as (PCA2) - (PCA1) is within a selected range of K where K is a predicted differential amplitude the determination is made that no amplitude artifact is present and the amplitude values are valid;
   (f) continuing to bleed down the cuff pressure until a peak value of PCA is reached and the amplitude begins to decrease;
   (g) continuing to monitor the PCA for a selected period and comparing the successive values of amplitude with the previously observed peak value to determine that said peak value has, in fact, been reached in that at the end of said selected period, the amplitudes have all been less than said peak values; and
   (h) determining the value of the cuff pressure at the time of said peak value of PCA and recording this value of cuff pressure as the mean arterial pressure.

2. The method as in claim 1 including;
analyzing the amplitude of pressure oscillations and of cuff pressures and determining, as the cuff pressure is reuced by bleeding down from a value greater than systolic, the value of cuff pressure at substantially the time at which the PCA starts to rise above a threshold; and
recording this value of cuff presure as the systolic pressure.

3. The method as in claim 1 and including:
the additional steps of continuing the bleeding down of cuff pressure and, as the PCA stops decreasing at increments above a threshold, determining the value of cuff pressure; and
recording this value as the diastolic pressure.

4. The method as in claim 3 and including the additional steps of dumping the air from the cuff and removing the cuff from the body of said person.

5. The method as in claim 1 including:
   (a) determining the periods of oscillation of cuff pressure at a selected Nth heartbeat and at a selected (N+1th) heartbeat and determining the amplitude of oscillation at the Nth and N+1th heartbeat;
   (b) determining the ratios of successive periods and the ratios of successive amplitdues;
   (c) determining whether the ratios of step (b) vary from preselected range values, thereby indicating whether artifacts may be present in one or the other pairs of values;
   (d) when said ratios determined in step (c) vary from preselected values, stopping the bleeding of cuff pressure and holding the cuff pressure constant and continuing the measurement of period and amplitude of oscillation with successive heartbeats until the successive measurements show substantial ratios within said preselected range values; and
   (e) restarting the bleeding of cuff pressure.

6. The method as in claim 1 including:
   (k) continuing to bleed down the cuff pressure and, as the amplitude of cuff pressure oscillations stops decreasing at increments above a threshold, determining the value of such cuff pressure at such time; and (i) using the value of cuff pressure determined in step (k) as the person's diastolic pressure.

7. Apparatus for automatically determining by noninvasive measurements the systolic-diastolic and mean arterial pressure of a person, including:
   (a) a gas pressure cuff means for placement around a portion of said person's body having means to inflat said cuff means to a pressure higher than the systolic pressure of said person;
   (b) means to bleed down said cuff pressure at a selected rate means to hold said cuff pressure constant at the pressure in said cuff means at a selected time, and means to dump all pressure from said cuff means, whereby the cuff pressure will at any time be constant, bleeding down, increasing, or substantially zero;
   (c) pressure sensor means connected to said cuff means for determining a first cuff pressure which is the cuff pressure signal measured directly at the cuff means;
   (d) means for digitizing said cuff pressure signal;
   (e) means to filter said cuff pressure through a low band pass filter in the range of 1-8 Hz. to provide an oscillatory signal part of said cuff pressure, whereby the second cuff pressure is the oscillating component of the cuff pressure and as the cuff pressure is bled down, the second cuff pressure will show increasingly high amplitudes of oscillation of cuff pressure;
   (f) means to store the contemporaneous values of the first cuff pressure and second cuff pressure as said first cuff pressure is bled down; and
   (g) means to measure the values of oscillation period and amplitude of said second cuff pressure of a succeeding heartbeat;
   (h) means to compare the periods and amplitude measurements; and
   (i) means to take the differential amplitude of the two succeeding values of amplitude of oscillation of said second cuff pressure and comparing said differential values with a predicted value K.

8. A method for automatically determining the blood pressure of a person, comprising the steps of:
   (a) placing a pressure cuff around an extremity of said person's body and inflating said cuff to a selected cuff pressure;
   (b) measuring and storing the amplitude of cuff pressure oscillations with each heartbeat of said person;
   (c) bleeding down the cuff pressure at a selected substantially linear rate and recording the first amplitude of oscillation at a first cuff pressure;
   (d) repeating step (c) for a second lower cuff pressure on the succeeding heartbeat to obtain a second amplitude of oscillation at a second cuff pressure;
   (e) for each heart beat prdicting the amplitude of oscillation for the next heart beat;
   (f) determining the different in amplitude of oscillation of the next heart beat with the predicted amplitude;
   (g) determining whether the difference in measured amplitude of oscillation of the succeeding heart beat and the predicted amplitude is within a preselected range;
   (h) if the difference determined in step (g) is within said predicted range, continuing to bleed down the cuff pressure, and if the difference determined in step (g) is not within said predicted range, terminating the cuff pressure bleed down until the difference is within said selected range and the continuing to bleed down the cuff pressure;
   (i) means of determining the blood pressure measurements of the person using the cuff pressure; and
   (j) continuing to bleed down the cuff pressure until the desired blood pressure measurements have been made.

9. A method as in claim 8 wherein step (j) is continued until a peak value for cuff pressure oscillation is reached and the amplitude begins to decrease;
   (k) continuing to monitor the value of cuff pressure oscillations and comparing the successive values of amplitude with the previously observed peak value to determine that aid peak value has, in fact been reached in that at the end of said selected period, the amplitudes have all been less than the said peak value; and
   (l) determining the value of the cuff pressure at the time of said peak value of the amplitude of cuff pressure oscillation and using this value of cuff pressure as the mean arterial pressure.

10. The method as in claim 8 including:
analyzing the amplitude of pressure oscillations and of cuff pressures and determining, as the cuff pressure is reduced by bleeding down from a value greater than systolic, the value of cuff pressure at substantially the time at which the amplitude of cuff pressure oscillations starts to rise above a threshold; and
recording this value of cuff pressure as the systolic pressure.

11. The method as in claim 8 including:
   (k) determining the periods of oscillation of cuff pressure at a selected Nth heartbeat and at a selected (N+1th) heartbeat;
   (l) determining the ratios of successive periods;
   (m) determining whether the ratios of step (l) vary from a preselected range value, thereby indicating whether artifacts may be present;
   (n) when said ratios determined in step (m) vary from preselected values, stopping the bleeding of cuff pressure and holding the cuff pressure constant and continuing the measurement of the period of heartbeats until the successive measurements shown ratios within said preselected range values; and
   (o) restarting the bleeding of cuff pressure.

* * * * *